United States Patent [19]
Pearson et al.

[11] Patent Number: 5,376,679
[45] Date of Patent: Dec. 27, 1994

[54] BICYCLIC OR TRICYCLIC BIOCIDAL COMPOUNDS

[75] Inventors: Michael Pearson, Sittingbourne; Andrew C. G. Gray, London; Thomas W. Naisby, Sittingbourne; William W. Wood, Sittingbourne; Susan J. Turner, Sittingbourne; Tarnia M. Machin, Sittingbourne, all of England

[73] Assignee: Shell Internationale Research Maatschappij B.V., Netherlands

[21] Appl. No.: 180,501

[22] Filed: Jan. 12, 1994

Related U.S. Application Data

[63] Continuation of Ser. No. 845,780, Mar. 5, 1992, abandoned, which is a continuation of Ser. No. 441,714, Nov. 27, 1989, abandoned.

[30] Foreign Application Priority Data

Nov. 29, 1988 [GB] United Kingdom ............... 8827850

[51] Int. Cl.$^5$ .............................................. A61K 31/35
[52] U.S. Cl. .................................... 514/456; 514/457; 514/469
[58] Field of Search ........................ 514/456, 457, 469

[56] References Cited

U.S. PATENT DOCUMENTS 3,991,204 11/1976 Pankavich ...................... 424/281
4,766,144 8/1988 Muller et al. .................. 514/457

FOREIGN PATENT DOCUMENTS 3012868 4/1978 Japan ............................. A01N 9/28
3038620 8/1978 Japan.

*Primary Examiner*—Marianne M. Cintins
*Assistant Examiner*—Russell Travers

[57] ABSTRACT

Compounds of the general formula

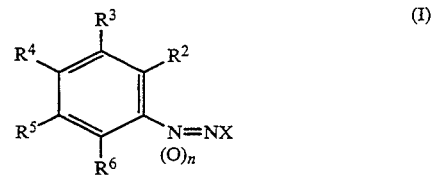

where $R^2$ and $R^3$ together, or $R^3$ and $R^4$ together, represent an optionally substituted hydrocarbyloxy chain; the ring is optionally substituted at any or each of the remaining sites $R^5$, $R^6$ and $R^2$ or $R^4$: n represents 0 or 1; and X represents a cyano group, a group —COOH or a salt, ester or amido derivative thereof; are biocidal, showing activity against fungi, yeast, bacteria and nematodes. Some such compounds, and intermediates therefore, are novel.

7 Claims, No Drawings

BICYCLIC OR TRICYCLIC BIOCIDAL COMPOUNDS

This application is a continuation of application Ser. No. 07/845,780, filed Mar. 5, 1992 now abandoned, which is a continuation of Ser. No. 07/441,714, filed Nov. 27, 1989, now abandoned.

This invention relates to novel bicyclic or tricyclic compounds having an azo substituent, to their use as fungicidal and/or bactericidal and/or nematicidal agents, to fungicidal and/or bactericidal and/or nematicidal compositions containing such compounds, and to the preparation of such compounds.

Calvatic acid, (4-(cyano-N,N,O-azoxy) benzoic acid) and a limited number of analogous compounds, have been investigated in respect of their antibacterial and antifungal properties. Thus, in Trans. Mycol. Soc. Japan, 23, p. 225-234, 1984, calvatic acid and its methyl ester are described as having antibacterial and antifungal activity. In Eur. J. Med. Chem—Chimica Therapeutica, Jan.-Feb. 1977—12 No. 1, p. 59-62, the preparation and screening of further analogues is described. The compounds made and tested were of the following formula:

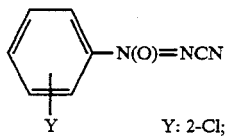

Y: 2-Cl; 3-Cl; 4-Cl
2-Br; 3-Br; 4-Br;
2-$NO_2$; 3-$NO_2$; 4-$NO_2$;
2-$OCH_3$; 3-$OCH_3$; 4-$OCH_3$;
H;
p-$N(CH_3)_2$

Antibacterial and antifungal properties of 4-carboxyphenylazoxycyanide-dimethylsulphoxide are described in Acta Crystallogr., Sect. B, 1975, B31(8) p. 2151-3.

The antibacterial properties of certain further compounds are described in Japanese Patent application (Kokai) J5 2071444 (Takara Shuzo KK). The compounds are said (in Chemical Abstract No. 87:167770) to be compounds of the formula given above, where X is 2-$CH_3$; 3-$CH_3$; 3-COOH; 3-Cl; 3,4-$Cl_2$; and 2,5-$CH_3$,Cl).

In the Journal of Antibiotics 6/1986, p. 864-8, the preparation and bactericidal and fungicidal screening of 2-(cyano-N,N,O-azoxy)benzoic acid is described but it is said to show no relevant activity against the tested fungi, and show low activity against bacteria.

In U.S. Pat. Nos. 4,558,040 and 4,550,121 there is described the miticidal activity of (2-alkyl-3,4-dihydro-2H-1-benzopyran-8-yl)diazenecarboxylic acid esters and (2-substituted-2,3-dihydrobenzofuran-7-yl)-diazenecarboxylic acid esters.

The present invention is based upon the discovery of the effectiveness of certain compounds, many of which are new, in combating fungi, including plant pathogenic fungi, bacteria and yeasts, and nematodes.

According to a first aspect of the present invention there is provided a method of combating a fungus, and/or bacterium, and/or yeast, and/or nematode, at a locus, which comprises treating the locus with a compound of the general formula

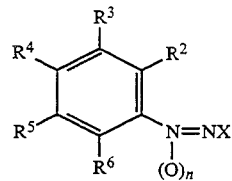

where $R^2$ and $R^3$ together, or $R^3$ and $R^4$ together, represent an optionally substituted hydrocarbyloxy chain; the ring is optionally substituted at any or each of the remaining sites $R^5$, $R^6$ and $R^2$ or $R^4$; n represents 0 or 1; and X represents a cyano group, a group —COOH or a salt, ester or amido derivative thereof.

The term "hydrocarbyloxy chain" is used herein to denote respectively a carbon atom chain interrupted within the chain by one or more (but preferably one only) oxygen atom. A (or the) oxygen atom is preferably located at one end of the chain.

Optional substituent(s) of the hydrocarbyloxy chain are, suitably, optionally substituted alkyl group(s), preferably alkyl group(s) optionally substituted by one or more (preferably one) halogen atom(s) or hydroxy or alkoxy group(s); optionally substituted phenyl group(s); an alkylene group, preferably —$(CH_2)_4$—, across adjacent carbon atoms of the hydrocarbyloxy chain; or group(s) =O.

Unless otherwise specified in this specification, an alkyl group may be linear or branched and suitably contains up to 10, preferably up to 6, and most preferably up to 4, carbon atoms, preferred examples being methyl and ethyl.

Unless otherwise stated in this specification, when any groups are designated as being optionally substituted, the substituent groups which are optionally present may be any of those customarily employed in the development of biocidal compounds, and/or the modification of such compounds to influence their structure/activity, persistence, penetration or other property. In relation to an alkyl group or alkylene or hydrocarbyloxy chain, specific examples of such substituents include halogen, especially fluorine, chlorine or bromine atoms, and phenyl, cyano, amino, mono- or di-($C_{1-4}$ alkyl)amino and $C_{1-4}$ haloalkyl groups, and groups of the general formula $MR^7$ and $CO.GR^7$ where M represents an oxygen or sulphur atom or a sulphenyl or sulphonyl group, G represents an oxygen or sulphur atom and $R^7$ represents a hydrogen atom, a $C_{1-8}$, expecially $C_{1-4}$, alkyl group, a $C_{1-4}$ haloalkyl group or a phenyl group. In relation to a phenyl moiety, optional substituents include halogen atoms, for example fluorine, chlorine, bromine and iodine atoms, and nitro, cyano, amino, mono- or di-($C_{1-4}$)-alkylamino, $C_{1-4}$ alkyl, $C_{2-4}$ alkenyl, $C_{2-4}$ alkynyl and $C_{1-4}$ haloalkyl (especially $CF_3$) groups, and groups of formula $MR^7$ or $CO.GR^7$ as defined above.

Accordingly it is preferred that $R^2$ and $R^3$ together, or $R^3$ and $R^4$ together, represent a hydrocarbyloxy chain optionally substituted by one or more moieties independently selected from halogen atoms, optionally substituted alkyl or phenyl groups, or cyano, amino, mono- or di-($C_{1-4}$ alkyl)amino or $C_{1-4}$ haloalkyl groups, or groups =O; or, across adjacent carbon atoms, an optionally substituted alkylene group; and groups of the general formula $MR^7$ and $CO.GR^7$ where M represents an oxygen or sulphur atom or a sulphenyl or sulphonyl group, G represents an oxygen or sulphur atom and $R^7$ represents a hydrogen atom, a $C_{1-4}$ alkyl group, a $C_{1-4}$ haloalkyl group or a phenyl group; and each of $R^6$, $R^5$ and $R^2$ or $R^4$ independently represents a hydrogen or halogen atom, or a nitro, cyano, amino, mono- or di-$C_{1-4}$ alkylamino, $C_{1-4}$ alkyl, $C_{2-4}$ alkenyl, $C_{2-4}$ alkynyl and $C_{1-4}$ haloalkyl group, or a group of formula $MR^7$ or $CO.GR^7$ as defined above.

Preferably, the hydrocarbyloxy chain is unsubstituted or substituted by 1-2 alkyl, haloalkyl, hydroxyalkyl or alkoxyalkyl groups, or by one alkylene group —$(CH_2)_4$— across adjacent carbon atoms, or by a group =O.

A hydrocarbyloxy chain preferably has 3 or 4 chain atoms. Preferred hydrocarbyloxy chains may be represented by oxyalkylene and oxyalkenylene chains. Within the ambit of the term "oxyalkenylene" as used herein are chains in which the pi electrons form part of a resonance electron system. When the chain is oxyalkenylene the chain may form, with the phenyl ring, a fused heteroaromatic ring system.

Preferred oxyalkylene and oxyalkenylene chains are based upon these structures (side atoms/groups not shown):

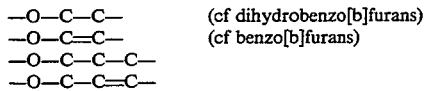

Particularly preferred oxyalkylene or oxyalkenylene chains are:

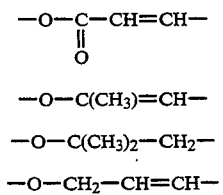

Optional substituents $R^5$, $R^6$ and $R^2$ or $R^4$ are preferably selected from halogen atoms and alkyl and alkoxycarbonyl groups, especially chlorine, methyl and methoxycarbonyl. Most preferably, the sites $R^5$, $R^6$ and $R^2$ or $R^4$ are all unsubstituted, or only one such site is substituted.

Preferably n represents 1.

Preferably, X represents a cyano group, a group COOH or a group —COOZ where Z represents a $C_{1-4}$ alkyl, alkenyl or alkynyl group, for example methyl, ethyl, allyl or propargyl. Most preferably, X represents a methoxycarbonyl or, especially, a cyano group.

In the method of the invention as described above the locus may be an agricultural or horticultural locus, for example plants subject to attack, seeds of such plants or the medium in which such plants are growing or are to be grown, or a non-living organic locus such as crude oil, an oil-derived liquid fuel, or lubricant, or a paint, detergent or textile. In relation to an agricultural or horticultural locus, compounds of the present invention have been shown to exhibit activity against a range of important fungi, including vine downy mildew, vine grey mould, wheat leafspot, barley powdery mildew, tomato early blight, wheat eyespot, seedling wheat blight and wheat brown rust, and against the rice root nematode *Meloidogyne graminicola*. Such a locus may suitably be treated with a compound I at an application rate in the range of 0.05-4 kg/ha, preferably 0.1-1 kg/ha. In relation to a non-agrochemical locus, compounds of the present invention have been shown to exhibit activity against certain filamentous fungi, gram-positive and gram-negative bacteria (including the sulphate-reducing bacterium *Desulfovibrio sp.*) and the yeast *Saccaromyces cerevisiae*.

The invention further provides the use as a fungicide and/or bactericide, and/or yeasticide, and/or nematicide, of a compound of the general formula I as defined in any of the above statements.

As mentioned above compounds of formula I in which X represents a cyano group are preferred, such compounds being of particularly interesting activity. Moreover, such compounds, along with certain other compounds, are believed to be novel. Accordingly, a further aspect of the invention provides compounds of the general formula I, as defined in any of the foregoing statements, per se, provided that X does not represent an alkoxycarbonyl group.

In a preferred novel class of compounds, X represents a cyano group.

Further in accordance with the invention there is provided a biocidal composition which comprises a carrier and, as active ingredient, a novel compound of general formula I, as defined above.

A carrier in a composition according to the invention is any material with which the active ingredient is formulated to facilitate application to the locus to be treated or to facilitate storage, transport or handling. A carrier may be a solid or a liquid, including a material which is normally gaseous but which has been compressed to form a liquid, and any of the carriers normally used in formulating biocidal compositions may be used. Preferably, compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emusifiable concentrates, emulsions, suspension concentrates and aerosols. Wettable powders usually contain 25,50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10% w of active ingredient. Granules are usually prepared to have a size between 10 and 100 BS mesh (1.676–0.152 mm), and may be manufactured by agglomeration or impregnation techniques. Generally, granules will contain 0.5–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion, inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick "mayonnaise"-like consistency.

The composition of the invention may also contain other ingredients, for example other compounds possessing herbicidal, insecticidal or fungicidal properties.

In accordance with a further aspect of the invention there is provided a process for the preparation of a novel compound, as defined above, of the general formula I, which comprises reacting a compound of the general formula

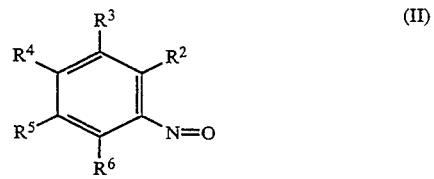

(II)

with cyanamide, to form a compound of formula I wherein n is 1 and X represents a cyano group; and optionally derivatising that compound to produce a further novel compound of formula I.

Suitably, the reaction takes place in the presence of an organic solvent, preferably a halogenated hydrocarbon, for example chloroform, and in the presence of iodobenzene diacetate. The reaction is preferably effected at a temperature in the range −20° C. to 50° C.

Derivatisation of the compound of formula I may for example, be effected by standard hydrolysis, in the presence of a strong acid or a strong base, to convert the cyano group to a carboxy group, or, stopping the reaction at an intermediate stage, an amido group.

Esters, which are not a novel class of compounds because of the disclosure of U.S. Pat. Nos. 4,558,040 and 4,550,121, may be prepared by standard esterification of the resultant carboxylic acid or by acid alcoholysis of the cyano compound to form the acid salt of the imidate ester, which is reacted with water, suitably at ambient temperature, to yield the ester. Alternatively, esters may be prepared by the following route, described in greater detail in U.S. Pat. Nos. 4,558,040 and 4,550,121, (Ar representing the aryl group):

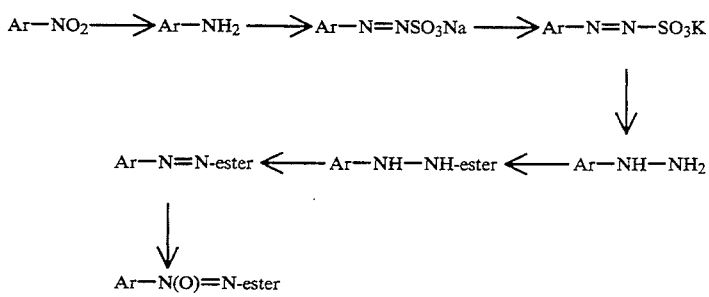

The latter two compounds may be converted to other compounds of formula I, for example amides, acids and nitriles, by standard methods.

A compound of formula II may be prepared as follows:

$$\text{(III)} \xrightarrow{A} \text{(III, NHOH)} \xrightarrow{B} \text{(II, N=O)}$$

with pathway (c) connecting back.

$$\text{(I): Ar-N=N-CN with (O)}_n$$

Reaction A may, for example, be effected by reaction of the nitro compound with hydrazine hydrate, in the presence of a hydrogen transfer catalyst, for example rhodium on carbon, suitably in the presence of an inert polar organic solvent, for example tetrahydrofuran, preferably with cooling; or be effected using water, stannous chloride as reducing agent, an inert, polar organic solvent, for example tetrahydrofuran, under an inert atmosphere, for example nitrogen, in the presence of sodium acetate, suitably at ambient temperature.

Reaction B may suitably be effected by treatment of the hydroxylamine derivative with an oxidising agent, for example an $Fe^{3+}$ compound, suitably ferric chloride. The reaction may be effected in a mixed water/polar organic solvent, preferably with cooling.

Reaction C may be effected by irradiating the nitro compound, which is preferably dissolved in an inert organic solvent, for example benzene. The irradiation may be effected using a medium pressure mercury lamp.

The nitro starting materials are known or else may be prepared from known compounds by standard methods. The hydroxylamine and nitroso derivatives of the general formulae III and II respectively are believed to be novel and they, and the methods for their preparation, constitute further aspects of the invention.

Novel compounds of formula I in which n is 0 may be made by an analogous method to that described in U.S. Pat. No. 291,046 and Med. Chem- Chim.Ther., 1982-17, No. 5, p. 482-4, wherein diazotisation of an amine compound is carried out, and the resulting diazotised compound is cyanurated, in the following manner.

$$\text{Ar-NH}_2 \xrightarrow{D} \text{Ar-N}_2^+ X^- \xrightarrow{E}$$

(IV)

where $X^-$ is an anion derived from a mineral acid. Optionally, a resultant compound I may be oxidised under standard conditions to yield a compound of general formula I wherein n is 1.

For reaction D, standard diazotisation conditions are employed, for example a low temperature, suitably 0°-20° C., and sodium nitrite in an aqueous mineral acid.

For reaction E, cyanuration is suitably effected by treating the compound of general formula IV with an alkali metal cyanide, for example sodium cyanide, suitably at a low temperature, for example −20° to +20° C., removing the aqueous layer, adding a halogenated hydrocarbon, for example carbon tetrachloride, and heating the organic layer, suitably at a temperature in the range 40°-100° C., preferably under reflux.

Steps D and E and the compounds of general formula IV are believed to be new and constitute further aspects of the invention.

Other methods suitable for preparing compounds of formula I, and further descriptions of the methods described herein, may be found in The Journal of Antibiotics, Jan. 1975, p. 87-90 and June 1986, p. 864-868; in Eur. J. Med. Chem. -Chim. Ther., 1982, 17, No. 5, p. 482-484, and 1980, 15, No. 5, p. 475-478, and 1977, 12, No. 1, p. 59-62; in J. Chem. Soc., Chem. Commun., 1984, p. 323-324; in Chem. Ind. (Milan), 1977, 59(5), p. 385; in Gazetta Chimica Italiana, 106, 1976, p. 1107-1110; in Tetrahedron Letters, No. 38, 1974, p. 3431-3432; and in U.S. Pat. Nos. 4,558,040 and 4,550,121.

The invention will now be further illustrated by the following examples.

EXAMPLE 1

$$\text{NCN=N-(coumarin with N-oxide)}$$

(a) To a stirred solution, under nitrogen, at room temperature, of 6-nitro coumarin (47.25 g: 0.25 moles) in tetrahydrofuran (1,875 lit.) was added water (150 ml) followed by sodium acetate (205 g: 2.5 moles) to give a yellow suspension. A slight exotherm was observed, the temperature rising from 20° C. to 25° C.

Solid stannous chloride (282 g: 1.25 moles) was added in one aliquot, the temperature rising to 32° C. over 10 mins, and self maintaining this temperature for 30 mins, then gradually cooling to room temperature. The reaction mixture was stirred overnight at room temperature and filtered to give a clear pale yellow solution of the hydroxylamine in tetrahydrafuran.

(b) The solution from above was added dropwise over 1 hr. at 0° C. to a stirred solution of ferric chloride hexahydrate (125 g: 0.77 mole) in water (1.875 lit.) to give a pale green suspension. The reaction mixture was stirred for a further 45 mins, at 0° C. The solution was extracted with dichloromethane (4×400 ml) and used in the next stage.

(c) To the above solution containing the nitroso compound was added cyanamide (21 g: 0.5 mole). The suspension was cooled to 0° C. and a solution of iodobenzene diacetate (87.5 g: 0.27 mole) in dichloromethane (500 ml) added dropwise over 10 mins, the green solution turning brown. The solution was filtered through "HYFLO" (Trade Mark), dried over magnesium sulphate and the solvent removed. The product was purified by chromatographing on a silica column eluting with 5% ethyl acetate/toluene. Yield 50% (based on the nitro coumarin).

|  | Analysis |  |  |
|---|---|---|---|
| $C_{10}H_5N_3O_3$ calc. % | 55.8 C | 2.3 H | 19.5 N |
| found % | 55.5 | 2.4 | 19.5 |

Further compounds were prepared according to procedures similar to those described in the preamble to the specification and in Example 1. Data on these compounds are set out in Table 1 below. In Table 1, reference is made to a compound of the following general formula:

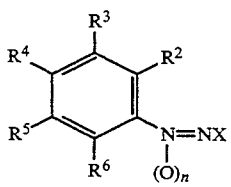

(II)

In Table 1, codes are used to identify hydrocarbyloxy groups —$R^2$—$R^3$— or —$R^3$—$R^4$—, as follows: (the left-hand bond shown below being connected to the lower denomination group R, i.e., $R^2$ of —$R^2$—$R^3$— and $R^3$ of —$R^3$—$R^4$—). The symbol — indicates no substitution.

A: —O—C(CH$_3$)$_2$—CH$_2$—

B: —O—CH(CH$_3$)—CH(CH$_3$)—

C: —O—CH(CH$_3$)—CH$_2$—

D: —O—CH(C$_2$H$_5$)—CH$_2$—

E: —O—CH(CH$_2$Cl)—CH$_2$—

F: —O—CH(CH$_2$OH)—CH$_2$—

G: —O—CH(CH$_3$)—CH$_2$—CH$_2$—

H: —O—C(CH$_3$)$_2$—CH$_2$—CH$_2$—

I: —O—C(CH$_3$)=CH—

J: —O—C=C—
        \\(CH$_2$)$_4$/

K: —O—C(CH$_3$)=C(CH$_3$)—

L: —O—C(C$_2$H$_5$)=CH—

M: —O—C(nC$_4$H$_9$)=CH—

N: —O—C(C$_6$H$_5$)=CH—

O: —CH=C(CH$_3$)—O—

P: —C=C—O—
        \\(CH$_2$)$_4$/

Q: —CH=C(C$_6$H$_5$)—O—

R: —O—CH$_2$—CH=CH—

S: —O—C(CH$_3$)$_2$—CH=CH—

T: —CH=CH—CH$_2$—O—

U: —O—CH(CH$_2$OCH$_3$)—CH$_2$—

V: —O—CH(CH$_3$)—CH=CH—

TABLE 1

| Ex. No. | $R^2$ | $R^3$ | $R^4$ | $R^5$ | $R^6$ | X | n | Analysis CHN Calc % Found % | mp/bp (°C.) | m/e |
|---|---|---|---|---|---|---|---|---|---|---|
| 2 | A | — | — | — | — | CN | 1 | 60.8 5.1 19.3 / 60.7 5.1 18.5 | 135 | 217 |
| 3 | A | — | CH$_3$ | — | — | CN | 1 | 62.3 5.6 18.2 / 63.0 5.8 18.1 | 143 | 231 |
| 4 | A | — | — | Cl | — | CN | 1 | 52.5 4.0 16.7 / 52.3 4.0 16.4 | 117–120 | 251.5 |
| 5 | B | — | — | Cl | — | CN | 1 | 52.5 4.0 16.7 / 52.7 4.0 16.5 | 68–70 | 251.5 |
| 6 | C | — | — | Cl | — | CN | 1 | 50.5 3.3 17.7 / 50.6 3.3 17.5 | 106 | 237.5 |
| 7 | A | — | — | CH$_3$ | — | CN | 1 | 62.8 5.7 18.2 / 62.3 5.6 18.2 | 144 | 231 |
| 8 | D | — | — | — | — | CN | 1 | 63.1 5.6 20.0 / 61.2 5.4 19.0 | 88 | 217 |
| 9 | B | — | — | — | — | CN | 1 | 60.8 5.1 19.3 / 60.1 5.0 18.9 | 76 | 217 |

TABLE 1-continued

| Ex. No. | $R^2$ | $R^3$ | $R^4$ | $R^5$ | $R^6$ | X | n | Analysis CHN Calc % Found % | | | mp/bp (°C.) | m/e |
|---|---|---|---|---|---|---|---|---|---|---|---|---|
| 10 | E | — | — | Cl | — | CN | 1 | 44.1 | 2.5 | 15.4 | 100–103 | 272 |
|    |   |   |   |    |   |    |   | 44.1 | 2.5 | 15.2 |         |     |
| 11 | F | — | — | Cl | — | CN | 1 | 47.3 | 3.2 | 16.5 | 100–102 | 253.5 |
|    |   |   |   |    |   |    |   | 46.7 | 3.2 | 16.1 |         |     |
| 12 | F | — | — | — | — | CN | 1 | 54.8 | 4.1 | 19.2 | 90–93 | 219 |
|    |   |   |   |    |   |    |   | 53.6 | 4.4 | 20.6 |       |     |
| 13 | E | — | — | — | — | CN | 1 | 50.5 | 3.4 | 17.7 | 122 | 237.5 |
|    |   |   |   |    |   |    |   | 50.3 | 3.4 | 17.6 |     |       |
| 14 | G | — | — | — | — | CN | 1 | 60.8 | 5.1 | 19.4 |     | 217 |
|    |   |   |   |    |   |    |   | 61.1 | 5.2 | 18.0 |     |     |
| 15 | H | — | — | Cl | — | CN | 1 | 54.2 | 4.5 | 15.8 | 72 | 265.5 |
|    |   |   |   |    |   |    |   | 52.7 | 4.4 | 15.3 |    |       |
| 16 | I | — | — | — | — | CN | 1 | 59.7 | 3.5 | 20.9 | 232 | 201 |
|    |   |   |   |    |   |    |   | 59.8 | 3.5 | 20.7 |     |     |
| 17 | J | — | — | — | — | CN | 1 | 64.8 | 4.5 | 17.4 | 105–107 | 241 |
|    |   |   |   |    |   |    |   | 63.8 | 4.4 | 17.1 |         |     |
| 18 | K | — | — | — | — | CN | 1 | 61.4 | 4.2 | 19.6 | 127–130 | 215 |
|    |   |   |   |    |   |    |   | 61.3 | 4.2 | 19.8 |         |     |
| 19 | L | — | — | — | — | CN | 1 | 61.4 | 4.2 | 19.6 | 88–90 | 215 |
|    |   |   |   |    |   |    |   | 62.0 | 4.3 | 20.4 |       |     |
| 20 | M | — | — | — | — | CN | 1 | 64.2 | 5.4 | 17.3 | 60–62 | 243 |
|    |   |   |   |    |   |    |   | 63.8 | 5.4 | 17.4 |       |     |
| 21 | N | — | — | — | — | CN | 1 | 68.5 | 3.4 | 16.0 | 140–143 | 263 |
|    |   |   |   |    |   |    |   | 68.5 | 3.3 | 16.1 |         |     |
| 22 | I | F | — | — | — | CN | 1 | 54.8 | 2.8 | 19.2 | 100–103 | 219 |
|    |   |   |   |    |   |    |   | 55.3 | 3.0 | 19.0 |         |     |
| 23 | — | O | — | — | — | CN | 1 | 59.7 | 3.4 | 20.8 | 115–117 | 201 |
|    |   |   |   |    |   |    |   | 59.6 | 3.2 | 20.8 |         |     |
| 24 | — | P | — | — | — | CN | 1 | 64.8 | 4.5 | 17.5 | 149–151 | 241 |
|    |   |   |   |    |   |    |   | 64.8 | 4.5 | 18.7 |         |     |
| 25 | — | Q | — | — | — | CN | 1 | 68.4 | 3.4 | 15.9 | 188–191 | 263 |
|    |   |   |   |    |   |    |   | 66.5 | 3.4 | 15.8 |         |     |
| 26 | R | — | — | Cl | — | CN | 1 | 51.0 | 2.5 | 17.8 | 151 | 235.5 |
|    |   |   |   |    |   |    |   | 51.5 | 2.8 | 16.6 |     |       |
| 27 | S | — | — | — | — | CN | 1 | 62.4 | 4.8 | 18.2 | 60 | 229 |
|    |   |   |   |    |   |    |   | 62.9 | 4.8 | 18.3 |    |     |
| 28 | — | T | — | — | — | CN | 1 | 59.7 | 3.5 | 20.9 | 128 | 201 |
|    |   |   |   |    |   |    |   | 60.0 | 3.6 | 19.3 |     |     |
| 29 | S | — | — | F | — | CN | 1 | 58.3 | 4.1 | 17.0 | 65 | 247 |
|    |   |   |   |    |   |    |   | 59.1 | 4.6 | 16.0 |    |     |
| 30 | R | — | — | $C_6H_5$ | — | CN | 1 | 69.3 | 4.0 | 15.2 | 152 | 277 |
|    |   |   |   |          |   |    |   | 67.2 | 4.0 | 14.3 |     |     |
| 31 | A | — | — | — | — | $CO_2CH_3$ | 0 | | | | 57–59 | |
| 32 | A | — | — | $CH_3$ | — | $CO_2CH_3$ | 0 | | | | 66–68 | |
| 33 | C | — | — | $CH_3$ | — | $CO_2CH_3$ | 0 | | | | 82–84 | |
| 34 | C | Cl | — | $CH_3$ | — | $CO_2CH_3$ | 0 | | | | | |
| 35 | C | $CH_3$ | Cl | — | — | $CO_2CH_3$ | 0 | | | | 112–114 | |
| 36 | U | — | Cl | $CH_3$ | — | $CO_2CH_3$ | 0 | | | | 64–66 | |
| 37 | D | $CH_3$ | — | — | — | $CO_2CH_3$ | 0 | | | | red syrup | |
| 38 | A | $CH_3$ | — | — | — | CN | 0 | 66.9 | 6.1 | 19.5 | 155–160 (decomp.) | 215 |
|    |   |        |   |   |   |    |   | 67.0 | 5.9 | 19.2 |                   |     |
| 39 | G | $CH_3$ | — | — | — | $CO_2CH_2C{\equiv}CH$ | 0 | | | | 90–92 | |
| 40 | G | $CH_3$ | — | — | — | $CO_2CH_2CH{=}CH_2$ | 0 | | | | | |
| 41 | G | Cl | — | $CH_3$ | — | $CO_2CH_2C{\equiv}CH$ | 0 | | | | 97–99 | |
| 42 | G | Cl | — | $CH_3$ | — | $CO_2C_2H_5$ | 0 | | | | 90–92 | |
| 43 | A | — | — | — | — | $CO_2CH_3$ | 1 | | | | 77–80 | |
| 44 | A | — | — | $CH_3$ | — | $CO_2CH_3$ | 1 | | | | 86–89 | |
| 45 | C | — | — | $CH_3$ | — | $CO_2CH_3$ | 1 | | | | 82–84 | |
| 46 | G | $CH_3$ | — | — | — | $CO_2CH_3$ | 1 | | | | 92–94 | |
| 47 | V | — | — | — | — | CN | 1 | | | | | |
| 48 | R | — | $CO_2CH_3$ | — | — | CN | 1 | | | | | |

EXAMPLE B1

The fungicidal activity of compounds of the invention was investigated by means of the following tests.

(a) Direct Protectant Activity Against Vine Downy Mildew (*Plasmopara viticola;* Pvp)

The test is a direct protectant one, using a foliar spray. The lower surfaces of leaves of whole vine plants (cv *Cabernet Sauvignon*) are sprayed with a solution of active material in 1:1 v/v water/acetone containing 0.04% w "Triton X-155" (trade mark) (octylphenol polyoxyethylene surfactant), at a dosage of 1 kilogram of active material per hectare using a track sprayer which delivers 620 liters/ha, and after a subsequent 24 hours under normal glasshouse conditions the lower surfaces of the leaves are inoculated by spraying with an aqueous solution containing $10^4$ zoosporangia/ml. The inoculated plants are kept for 24 hours in a high humidity compartment, 5 days under normal glasshouse conditions and then returned for a further 24 hours to high humidity. Assessment is based on the percentage of leaf area covered by sporulation compared with that on control leaves.

(b) Direct Protectant Activity Against Vine Grey Mould (*Botrytis cinerea;* Bcp)

The test is a direct protectant one using a foliar spray and is effected as described under (a), with the difference that the leaves are inoculated by spraying with an aqueous solution containing $10^5$ conidia/ml.

(c) Activity Against Wheat Eyespot (*Pseudocercosporella herpotrichoides;* Ph)

The test is an in vitro one. Samples are prepared wherein 0.7 mls solution containing 2 mg active material dissolved in acetone is evenly dispersed in 20 ml molten half-strength potato dextrose agar (formed by dissolving 2 g potato extract, 10 g dextrose and 7.5 g agar in 1 liter of water and sterilising for 15 minutes and 121° C.) and the resulting 20 ml portions are allowed to set in 9 cm petri dishes. The concentration of active material in the resulting samples is 100 ppm. Upon setting, two plugs of 5 mm diameter taken from the advancing edge of a stock plate of a 3 to 4 week old culture of *P.herpotrichoides* on full strength potato dextrose agar, incubated at 20°–22° C. in darkness, are placed, equally spaced on the surface of each sample, mycelial side uppermost. The samples are incubated for 11 days at 20°–22° C. in darkness before assessment. Diametric growth is measured with the width of the plug subtracted and results compared with growth on a sample wherein 0.7 ml acetone containing no active material is dispersed in 20 ml half-strength potato agar.

(d) Activity Against Seedling Wheat Blight (*Fusarium culmorum;* Fs)

The test is an anti-sporulant one using a soil drench. Surface sterilised wheat seeds (var Waggoner) are inoculated by soaking in an aqueous suspension containing $7 \times 10^5$ spores/ml (60 mg seed per 80 ml suspension) at 22° C. for 6 hours. The seeds are then sown in pots (5 per pot) in sand at a depth of 1 cm. 1 day after inoculation and planting the active material is applied at a rate of 10 kg/ha by pouring on a soil drench (concentration 0.36 g/l active material in 12% v/v acetone/water) evenly over the sand. The pots are then transferred to a glasshouse, kept at 25° C. and watered sparingly. 21 days after inoculation the resulting seedlings are removed from the pots and their roots are gently washed. Visual assessment is made based on lesion development on stem base and upper roots in comparison with control seedlings.

(e) Activity Against Wheat Leafspot (*Leptosphaeria nodorum;* Ln)

The test is a direct antisporulant one, using a foliar spray. Leaves of wheat plants (cv Mardler), at the single leaf stage, are inoculated by spraying with an aqueous suspension containing $8 \times 10^5$ spores/mi. The inoculated plants are kept for 24 hours in a high humidity compartment prior to treatment. The plants are sprayed at a dosage of 1 kg of active material per hectare using a track sprayer as described under (a). After drying, the plants are kept for 5 days under normal glasshouse conditions, followed by assessment. Assessment is based on the percentage of leaf area covered by sporulation compared with that on leaves of control plants.

(f) Activity Against Barley Powdery Mildew (*Erysiphe graminis f.sp. hordei;* Eg)

The test is a direct antisporulant one, using a foliar spray. Leaves of barley seedlings, cultivar Golden Promise, are inoculated by dusting with mildew conidia one day prior to treatment with the test compound. The inoculated plants are kept overnight at glasshouse ambient temperature and humidity prior to treatment. The plants are sprayed at a dosage of 1 kg of active material per hectare using a track sprayer as described under (a). After drying, plants are returned to a compartment at ambient temperature and humidity for up to 7 days, followed by assessment. Assessment is based on the percentage of leaf area covered by sporulation compared with that on leaves of control plants.

(g) Activity Against Tomato Early Blight (*Alternaria Solani;* As).

The test is a direct protectant one using a foliar spray. The upper surfaces of leaves of young tomato plants are sprayed with a solution of active material as described in (a) above. After 24 hours under normal glasshouse conditions, the upper surfaces of the leaves are inoculated by spraying with an aqueous suspension containing $10^4$ spores/ml. The inoculated plants are kept for 72 hours in a high humidity compartment and are then removed to lower humidity (50–70% relative humidity). Assessment is made 8 days after inoculation.

(h) Activity Against Apple Powdery Mildew (*Podosphaera leucotricha;* Pl)

The test is a direct anti-sporulant one using a foliar spray. The upper surfaces of leaves of whole seedlings are inoculated by spraying with an aqueous suspension containing $10^5$ conidia/ml 2 days prior to treatment with the test compound. The inoculated plants are immediately dried and kept at glasshouse ambient temperatures and humidity prior to treatment. The plants are sprayed at a dosage of 1 kg of active material per hectare using a track sprayer as described under (a). After drying the plants are returned to a compartment at ambient temperature and humidity for up to 9 days, followed by assessment. Assessment is based on the percentage of the leaf area covered by sporulation compared with that on leaves of control plants.

(i) Activity Against Wheat Brown Rust (*Puccinia Recondita;* Pr)

The test is a direct protectant one using a foliar spray. Wheat seedlings (cv Brigand) are grown to the 1–1.5 leaf stage. The plants are then sprayed with the test compound at a dosage of 1 kg/ha using a track sprayer as described under (a). Test compounds are applied as solutions or suspensions in a mixture of acetone and water (50:50 v/v) containing 0.04% surfactant ("TWEEN 20"—Trade Mark).

18–24 hours after treatment, the seedlings are inoculated by spraying the plants from all sides with an aqueous spore suspension containing about $10^5$ spores/ml. For 18 hours after inoculation, the plants are kept in high humidity conditions at a temperature of 20°–22° C. Thereafter, the plants are kept in ambient glasshouse conditions, that is, in moderate relative humidity and at a temperature of 20° C.

The disease is assessed 10 days after inoculation on the basis of the percentage of the plant covered by sporulating pustules compared with that on the control plants.

(j) Antisporulant Activity Against Vine Downy Mildew (*Plasmopara viticola;* Pva)

The test is a direct antisporulant one using a foliar spray. The lower surfaces of leaves of whole vine plants (cv Cabernet Sauvignon) are inoculated by spraying with an aqueous suspension containing $10^4$ zoosporangia/ml 2 days prior to treatment with the test compound. The inoculated plants are kept for 24 hours in a high humidity compartment, and then 24 hours at glasshouse ambient temperature and humidity. When the plants are dry, infected leaves are sprayed on their lower surfaces with a solution of active material in 1:1 water/acetone containing 0.04% w/w "Triton X-155" (trade mark) (an octylphenol polyethoxylate surfactant). The spraying is carried out with a moving track sprayer with delivers 620 liter/ha, and the concentration of active material is calculated to give an application rate of 1 kg/ha. After spraying, the plants are returned to normal glasshouse conditions for 96 hours and are then transferred to the high humidity compartment for 24 hours to induce sporulation, prior to assessment. Assessment is visual and is based on the percentage of the leaf area covered by sporulation compared with that on control leaves.

(h) Activity Against Rice Leaf Blast (*Pyricularia oryzae;* Po)

The test is a direct eradicant one using a foliar spray. The leaves of rice seedlings (about 30 seedlings per pot) are sprayed with an aqueous suspension containing $10^5$ spores/ml 20–24 hours prior to treatment with the test compound. The inoculated plants are kept overnight in high humidity and then allowed to dry before spraying at a dosage of 1 kg of active material per hectare using a track sprayer as described under (a). After treatment the plants are kept in a rice compartment at 25°–30° C. and high humidity. Assessments are made 4–5 days after treatment and are based on the density of necrotic lesions and the degree of withering when compared with control plants.

The results of the above tests are given in Table 2 below:

TABLE 2

| Ex. No. | Pvp | Bcp | Ph | Fs | Ln | Eg | As | Pr | Other |
|---|---|---|---|---|---|---|---|---|---|
| 1 | 2 | 1 | 2 | 2 | 1 | | 2 | 2 | |
| 2 | 1 | 2 | 2 | 2 | | | | | |
| 3 | 2 | 1 | 2 | 1 | 1 | | 1 | | |
| 4 | 2 | | 2 | 2 | 1 | | | 2 | |
| 5 | 2 | | 2 | 2 | 1 | 1 | | 2 | Pva 2 |
| 6 | 2 | | 2 | 2 | 1 | | 1 | 2 | |
| 7 | 2 | | 1 | 1 | 1 | | | 2 | |
| 8 | | | 2 | 2 | 1 | 1 | | | |
| 9 | | | 2 | 2 | 1 | 1 | | | Pva 1 |
| 10 | 2 | | 2 | 2 | 1 | | | 2 | |
| 11 | 2 | | 2 | 2 | | | | 1 | |
| 14 | | | 2 | | | | | | |
| 15 | | | 2 | 2 | | | | | |
| 16 | 2 | 2 | 1 | 1 | | | 2 | 1 | |
| 17 | 2 | | 1 | 2 | 1 | | 1 | 1 | |
| 18 | 2 | | 1 | 2 | | 1 | 2 | 2 | |
| 19 | | | 1 | 1 | | 1 | 2 | 2 | |
| 20 | | | 2 | 1 | | | | 1 | |
| 21 | | 1 | | | | | | | |
| 22 | | 1 | 2 | 2 | 2 | | | | |
| 23 | | | 1 | 2 | | 1 | 1 | 2 | Pva 2 |
| 24 | 2 | | 1 | 1 | | | 2 | 1 | |
| 26 | 2 | 2 | 1 | 2 | 2 | | | 1 | Pva 2 |

TABLE 2-continued

| Ex. No. | Pvp | Bcp | Ph | Fs | Ln | Eg | As | Pr | Other |
|---|---|---|---|---|---|---|---|---|---|
| 27 | | | 2 | 2 | | | | | |
| 29 | | | 2 | 2 | | 1 | | | Pva 2 |
| 31 | | | 1 | 1 | | 1 | | | Pl 1 |
| 32 | 1 | | | | | | | | |
| 33 | 1 | | | | | 1 | | | Pva 1 |
| 35 | 1 | | 1 | | | | | | Pva 1 |
| 36 | 1 | | 2 | | | 2 | | | Pl 2 |
| 37 | 1 | | 1 | | | | 1 | | Pl 1 |
| 38 | 2 | | | | | | | | |
| 39 | | | | | 1 | 1 | | | |
| 40 | | | | | | 1 | | | Pl 2 |
| 41 | 1 | | | | | 1 | | | |
| 42 | | | | | | 2 | | | |
| 43 | | 1 | 2 | | | 2 | | | Pl 1 |
| 44 | 1 | | | | | 2 | | | |
| 45 | 1 | | | | | 2 | 1 | | |
| 46 | 2 | | 2 | | 2 | 2 | 2 | | Po 2 |

The fungicidal activity of certain of the compounds was investigated further, in secondary screening. These revealed that certain compounds were found to have particularly high activity against certain fungi. Example 1 was found to have high activity against As and Pvt (*Plasmopara viticola* as determined by a translaminar protectant test in which the upper surfaces of the leaves of whole vine plants are sprayed with a solution of the compound, and the lower leaves are then inoculated with the appropriate Zoosporangi); Example 16, against Bcp and Pvt; Example 26 and 37, against Pvt; Example 38, against Pvp; and Example 43, against Ph.

EXAMPLE B2

The activity of compounds of formula I in combating microorganisms was further demonstrated by tests against the following microorganisms.

| | |
|---|---|
| Gram positive bacteria | *Staphylococcus aureus* (Sa) (NCIB 6571) |
| | *Bacillus subtilis* (Bs) |
| Gram negative bacteria | *Escherichia coli* (Ec) (NCIB 9517) |
| | *Desulfovibrio sp.* (Dsp) mixed culture of sulphate-reducing bacteria ex Brent North Sea |
| Yeast | *Saccharomyces cerevisiae* (Sc) (ATCC 9763) |
| Filamentous fungi | *Aspergillus niger* (An) (CMI 17454) |
| | *Cladosporium resinae* (Cr) |
| | *Chaetomium globosum* (Chg) |

(NCIB—National Collection of Industrial Bacteria, Torry Research Station, P.O. Box 31, 135 Abbey Road, Aberdeen, Scotland. AB9 8DG).

(ATCC=American Type Culture Collection, 12301 Parklawn Drive, Rockville, Md. 20852, USA).

(CMI=Commonwealth Mycological Institute, Ferry Lane, Kew, Surrey, England).

Inocula of the above microorganisms were prepared as follows.

In respect of *S. aureus, B. subtilis* and *E. coli,* the microorganisms were cultured in 50 ml aliquots of a tryptone soya broth in 250 ml conical flasks at 30° C. on a rotary shaker at 200 rpm for 24 hours. Tryptone soya broth was prepared by adding 17 g pancreatic digest of casein, 3 g papaic digest of soyabean meal, 5 g of sodium chloride, 2.5 g of dipotassium hydrogen phosphate and 2.5 g of dextrose to 1 liter of distilled water, mixing and sterilising by autoclaving at 121° C. for 15 minutes. 1 ml aliquots of the resulting cultures were mixed with 99 ml of fresh tryptone soya broth and used as inocula for tests.

The sulphate reducing bacteria *Desulfovibrio sp.* were cultured in a modified Postgate's Medium B for 48 hours at 30° C. and used directly as an inoculum. The modified Postgate's Medium B consisted of 0.5 g dipotassium hydrogen phosphate, 1 g ammonium chloride, 1 g sodium sulphate, 5 g sodium lactate, 1 g yeast extract, 0.1 ml thioglycolic acid, 0.1 ml ascorbic acid, 0.5 g ferrous sulphate heptahydrate, 750 ml aged seawater and 250 ml distilled water, pH adjusted to 7.8, divided into aliquots and sterilised by autoclaving at 121° C. for 15 minutes.

Inocula of *S. cerevisiae* were prepared as for *S. aureus, B. subtilis* and *E. coli*, but using yeast malt broth in place of the typtone soya broth. The yeast malt broth was prepared by suspending 3 g yeast extract, 3 g malt extract, 5 g peptone and 10 g dextrose in 1 liter of distilled water, warming to achieve solution and sterilising by autoclaving at 121° C. for 15 minutes.

Inocula of the fungi *Aspergillus niger, Cladosporium resinae* and *Chaetomium globosum* were prepared containing $5 \times 10^5$ conidia/ml in a potato dextrose broth. The potato dextrose broth was prepared by suspending 4 g potato extract and 20 g dextrose in 1 liter of distilled water, warming to achieve solution, separating into aliquots and sterilising by autoclaving at 121° C. for 15 minutes.

Stock solutions of the various test compounds were prepared containing 10,000 ppm (1% w) compound in distilled water (in cases where the compound did not dissolve, up to 4% v/v acetone was included in the stock solution). Tests showed that such levels of acetone had no observable adverse effects on growth of the above listed microorganisms). Test procedures were as follows:

(i) Suphate-reducing Bacteria Test Dilution Series

Duplicate aliquots (9.9 ml) of dilution series from the stock solutions of each compound were prepared in a modified Postgate's Medium B described above. These contained 100 ppm compound. These were then inoculated with 0.1 ml of inoculum. After incubation at 30° C., the presence or absence of growth—as indicated by a blackening of the medium due to ferrous sulphide production—was recorded at 2, 5 and 10 days. Compounds active at 100 ppm were further tested at the lower concentrations of 5, 10, 25 and 50 ppm.

(ii) Dilution Series for Other Test Bacteria, Yeast and Filamentous Fungi

Dilution series from the stock solution of each compound were prepared in sterile distilled water. These contained 50, 100, 500 and 1000 ppm compound. To duplicate wells of a compartmentalised square petri dish 0.3 ml of each test compound concentration was added together with 2.7 ml of one of the microbial inocula described above. This gave final concentrations of the test compound of 5, 10, 50 and 100 ppm.

After incubation, in the dark, at 30° C. the wells were examined for the presence or absence of growth. Bacterial and yeast cultures were examined after 24 hours and 72 hours incubation and the fungi cultures after 3, 7 and 10 days.

By means of the above tests minimum inhibitory concentrations were determined for the various test compounds. These are given in Table 3 below.

TABLE 3

| Ex. No. | Minimum inhibitory concentration (ppm) | | | | | | | |
|---|---|---|---|---|---|---|---|---|
| | Sa | Bs | Ec | Dsp | Sc | An | Cr | Chg |
| 1 | >100 | 50 | >100 | 25 | 5–25 | 25 | 25–50 | 10 |
| 4 | 100 | 50 | >100 | >100 | >100 | 100 | 25 | >100 |
| 5 | >100 | 100 | >100 | >100 | 50 | 10 | 25 | 5–25 |
| 6 | 100 | 100 | >100 | 100 | 25 | 25 | 25 | 25 |
| 8 | >100 | >100 | >100 | >100 | 100 | 10 | 10 | <100* |
| 9 | >100 | 50 | >100 | 100 | 50 | 25 | 25 | 50 |
| 10 | >100 | >100 | >100 | 100 | >100 | 25 | 25 | <100* |
| 11 | 100 | 25 | 100 | 100 | 100 | 25 | 50 | 25 |
| 12 | >100 | 50 | 100 | 50 | >100 | >100 | 100 | 100 |
| 13 | 100 | 100 | 100 | >100 | 100 | 10 | 100 | 25 |
| 14 | >100 | >100 | >100 | 100 | 50 | 10 | 25 | <5 |
| 15 | >100 | 100 | >100 | >100 | 50 | 10 | >100 | >100 |
| 16 | >100 | >100 | >100 | 50–100 | 100 | 50 | >100 | NT |
| 17 | 100 | >100 | >100 | >100 | 50 | <5 | 25 | <100 |
| 18 | 5 | >100 | >100 | >100 | 100 | 100 | 100 | 100 |
| 20 | >100 | >100 | >100 | >100 | >100 | 100 | 100 | NT |
| 22 | >100 | 50–100 | >100 | 50 | 25 | 10 | 10–25 | 5 |
| 23 | >100 | 50 | >100 | 100 | 25 | 25 | 25 | <100* |
| 26 | 100 | 50 | >100 | 100 | >100 | 25–50 | 25–100 | 50 |
| 27 | >100 | >100 | >100 | 100 | >100 | 100 | 25 | <100* |
| 28 | >100 | 50–100 | >100 | 100 | 25 | 10–25 | 25–50 | 25 |
| 29 | >100 | 100 | >100 | >100 | 50 | 25–100 | 50–100 | 5–100 |

*only tested at 100 ppm.
NT: not tested

EXAMPLE B3

The nematicidal activity of the compounds of Example 17 and 23 was investigated. They were tested against the rice root nematode *Meloidogyne graminicola* in a water screen whereby the effect of retaining the nematodes in a dilute aqueous solution of the compounds was studied, and in a soil drench test in which the propensity of these nematodes to cause knots in the roots of grain sorghum *S. bicolor* was studied as a function of concentration of the compounds applied to the soil. The compounds were found to have activity against the nematodes in each of the tests. Thus in the water screen test it was determined that the minimum inhibitory concentration of the compound of Example 23 was 0.53 ppm.

We claim:

1. A biocidal composition which comprises a carrier and, as active ingredient, a biocidally effective amount of a compound of formula I

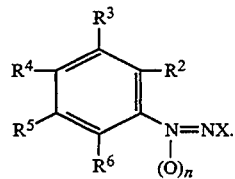

where $R^2$ and $R^3$ together, or $R^3$ and $R^4$ together, represent a $C_{3-4}$ oxyalkylene or oxyalkenylene chain optionally substituted by 1-2 $C_{1-6}$ alkyl, $C_{1-6}$ haloalkyl, $C_{1-6}$ hydroxyalkyl, $C_{1-6}$ alkoxyalkyl or phenyl groups, or by one alkylene group —(CH$_2$)$_4$— across adjacent carbon atoms, or by a group =O; the ring is optionally substituted at any or each of the remaining sites $R^5$, $R^6$ and $R^2$ or $R^4$, wherein each of $R^5$, $R^6$ and $R^2$ or $R^4$ independently represent a halogen atom or a $C_{1-6}$ alkyl or $C_{1-6}$ alkoxycarbonyl group; n represents 0 or 1; and X represents a cyano group.

2. A composition as claimed in claim 1 wherein the oxyalkylene or oxyalkenylene chain is selected from the group consisting of:

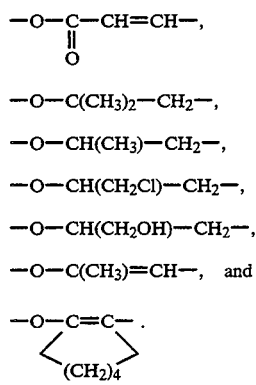

3. A composition as claimed in claim 1 wherein the oxyalkylene or oxyalkenylene chain is

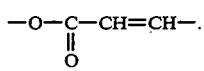

4. A method of combating a fungus, and/or bacterium, and/or yeast, and/or nematode, which method comprises treating plants subject to attack, seeds of such plants or the medium in which such plants are growing or are to be grown, crude oil, an oil-derived liquid fuel, lubricant, paint, detergent or textile with a compound of formula I

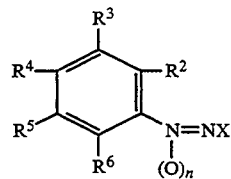

where $R^2$ and $R^3$ together, or $R^3$ and $R^4$ together, represent a $C_{3-4}$ oxyalkylene or oxyalkenylene chain optionally substituted by 1-2 $C_{1-6}$ alkyl, $C_{1-6}$ haloalkyl, $C_{1-6}$ hydroxyalkyl, $C_{1-6}$ alkoxyalkyl or phenyl groups, or by one alkylene group —(CH$_2$)$_4$— across adjacent carbon atoms, or by a group =O; the ring is optionally substituted at any or each of the remaining sites $R^5$, $R^6$ and $R^2$ or $R^4$, wherein each of $R^5$, $R^6$ and $R^2$ or $R^4$ independently represent a halogen atom or a $C_{1-6}$ alkyl or $C_{1-6}$ alkoxycarbonyl group; n represents 0 or 1; and X represents a cyano group.

5. A method as claimed in claim 4 wherein the oxyalkylene or oxyalkenylene chain is selected from the group consisting of:

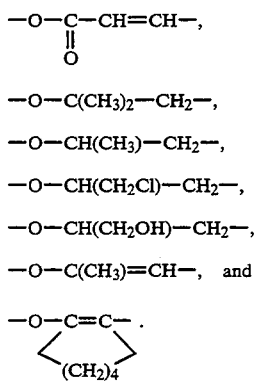

6. A method as claimed in claim 4 wherein the oxyalkylene or oxyalkenylene chain is

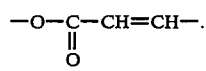

7. A compound as claimed in claim 4 wherein n is 1.

* * * * *